United States Patent
Miller

(10) Patent No.: US 9,730,840 B2
(45) Date of Patent: *Aug. 15, 2017

(54) METHODS AND DEVICES FOR COLLECTING BODY FLUIDS

(71) Applicant: Denise H. Miller, Alpharetta, GA (US)

(72) Inventor: Denise H. Miller, Alpharetta, GA (US)

( * ) Notice: Subject to any disclaimer, the term of this patent is extended or adjusted under 35 U.S.C. 154(b) by 229 days.

This patent is subject to a terminal disclaimer.

(21) Appl. No.: 14/792,802

(22) Filed: Jul. 7, 2015

(65) Prior Publication Data

US 2016/0000613 A1    Jan. 7, 2016

Related U.S. Application Data

(63) Continuation of application No. 13/656,516, filed on Oct. 19, 2012, now Pat. No. 9,078,786.

(51) Int. Cl.
| | | |
|---|---|---|
| *A61F 13/20* | (2006.01) | |
| *A61F 13/34* | (2006.01) | |
| *A61F 5/44* | (2006.01) | |
| *A61B 5/15* | (2006.01) | |
| *A61B 10/02* | (2006.01) | |

(Continued)

(52) U.S. Cl.
CPC .... *A61F 13/2042* (2013.01); *A61B 5/150015* (2013.01); *A61B 5/150358* (2013.01); *A61B 10/0291* (2013.01); *A61B 10/04* (2013.01); *A61F 5/44* (2013.01); *A61F 13/202* (2013.01); *A61F 13/2028* (2013.01); *A61F 13/34* (2013.01); *A61F 2013/2014* (2013.01); *A61F 2013/8476* (2013.01)

(58) Field of Classification Search
CPC ................ A61F 13/202; A61F 13/2028; A61F 13/2042; A61F 13/34; A61F 5/44; A61F 2013/2014; A61F 2013/8476; A61B 5/150015; A61B 5/150358; A61B 10/0291; A61B 10/04

See application file for complete search history.

(56) References Cited

U.S. PATENT DOCUMENTS

| | | | |
|---|---|---|---|
| 1,502,503 | A | 7/1924 | Hollrigl |
| 2,063,202 | A | 12/1936 | Spicer |
| 2,580,133 | A | 12/1951 | Sheen |

(Continued)

FOREIGN PATENT DOCUMENTS

GB         1394925 A        5/1975

OTHER PUBLICATIONS

Anderson. "Rupture of the Uterus; Treatment by Gauze Packing; Recovery" Proc R Soc Med. 1920; 13 (Obstet Gynaecol Sect) 188-191.

(Continued)

*Primary Examiner* — Kathryn E Ditmer
(74) *Attorney, Agent, or Firm* — Morris, Manning & Martin LLP

(57) ABSTRACT

Methods and devices for collection of fluids, including cells and cellular materials, from the uterus. A device having a central tubing member to which, at least, a flexible tubing member and an absorbable member are connected at least at one point. The absorbable member is connected to at least one portion of the central tubing member and to at least one portion of the flexible tubing member. The devices are useful in methods of collection of uterine fluids, including blood, cells and cellular material.

11 Claims, 4 Drawing Sheets

(51) Int. Cl.
*A61B 10/04* (2006.01)
*A61F 13/84* (2006.01)

(56) References Cited

U.S. PATENT DOCUMENTS

| | | |
|---|---|---|
| 3,216,420 A | 11/1965 | Smith |
| 3,312,215 A | 4/1967 | Silber |
| 3,452,749 A | 7/1969 | Riedell |
| 3,513,830 A | 5/1970 | Kalayjian |
| 3,659,596 A | 5/1972 | Robinson |
| 3,669,951 A | 6/1972 | Bien et al. |
| 3,699,951 A | 10/1972 | Zaffaroni |
| 3,699,962 A | 10/1972 | Hanke |
| 3,757,775 A | 9/1973 | Marco et al. |
| 3,757,782 A | 9/1973 | Aiken |
| 3,774,612 A | 11/1973 | Marco |
| 3,789,838 A | 2/1974 | Fournier et al. |
| 3,877,464 A | 4/1975 | Vermes |
| 3,918,444 A | 11/1975 | Hoff et al. |
| 3,958,561 A | 5/1976 | Bucalo |
| 3,971,367 A | 7/1976 | Zaffaroni |
| 3,996,933 A | 12/1976 | Gutnick |
| 4,014,748 A | 3/1977 | Spinner et al. |
| 4,014,987 A | 3/1977 | Heller et al. |
| RE29,231 E | 5/1977 | Leeds |
| 4,023,559 A | 5/1977 | Gaskell |
| 4,094,313 A | 6/1978 | Komamura et al. |
| 4,102,998 A | 7/1978 | Gutnick |
| 4,175,008 A | 11/1979 | White |
| 4,188,951 A | 2/1980 | Higuchi et al. |
| 4,200,090 A | 4/1980 | Drobish |
| 4,223,093 A | 9/1980 | Newman et al. |
| 4,237,893 A | 12/1980 | Michaels |
| 4,284,074 A | 8/1981 | Shaw, Jr. |
| 4,304,226 A | 12/1981 | Drobish et al. |
| 4,311,792 A | 1/1982 | Avery |
| 4,341,728 A | 7/1982 | Robertson et al. |
| 4,359,046 A | 11/1982 | Shaw, Jr. |
| 4,381,001 A | 4/1983 | Shaw, Jr. |
| 4,387,725 A | 6/1983 | Mull |
| 4,424,305 A | 1/1984 | Gould et al. |
| 4,467,806 A | 8/1984 | Bhiwandiwala et al. |
| 4,480,642 A | 11/1984 | Stoy et al. |
| 4,495,934 A | 1/1985 | Shaw, Jr. |
| 4,541,439 A | 9/1985 | Hon |
| 4,552,557 A | 11/1985 | Rangaswamy |
| 4,572,162 A | 2/1986 | Livesay et al. |
| 4,727,866 A | 3/1988 | Livesay et al. |
| 4,821,741 A | 4/1989 | Mohajer |
| 4,867,176 A | 9/1989 | Lash |
| 5,065,772 A | 11/1991 | Cox, Jr. |
| 5,083,572 A | 1/1992 | Pokorny |
| 5,169,385 A | 12/1992 | Turnbull |
| 5,185,270 A | 2/1993 | Senyei et al. |
| 5,273,054 A | 12/1993 | Walker |
| 5,555,896 A | 9/1996 | Cimber |
| 5,573,007 A | 11/1996 | Bobo, Sr. |
| 5,656,013 A | 8/1997 | Yoon |
| 5,713,369 A | 2/1998 | Tao et al. |
| 5,720,299 A | 2/1998 | Theodoru et al. |
| 5,782,800 A | 7/1998 | Yoon |
| 5,827,248 A | 10/1998 | Crawford |
| 5,840,055 A | 11/1998 | Sgro |
| 5,908,829 A | 6/1999 | Kelly |
| 5,912,006 A | 6/1999 | Bockow et al. |
| 6,045,786 A | 4/2000 | Cone et al. |
| 6,048,534 A | 4/2000 | Siler-Khodr |
| 6,066,132 A | 5/2000 | Chen et al. |
| 6,119,696 A | 9/2000 | Turin |
| 6,139,570 A | 10/2000 | Saadat et al. |
| 6,355,235 B1 | 3/2002 | Cone et al. |
| 6,423,038 B1 | 7/2002 | Vancaillie |
| 6,440,445 B1 | 8/2002 | Nowak et al. |
| 6,570,052 B2 | 5/2003 | Zadini et al. |
| 6,582,389 B2 | 6/2003 | Buzot |
| 6,602,218 B2 * | 8/2003 | Yoon ............... A61B 17/00234 604/1 |
| 6,702,759 B2 | 3/2004 | Pevoto |
| 6,708,056 B2 | 3/2004 | Duchon et al. |
| 7,041,310 B2 | 5/2006 | Yui et al. |
| 7,053,077 B1 | 5/2006 | Elger et al. |
| 7,105,007 B2 | 9/2006 | Hibler |
| 7,204,824 B2 | 4/2007 | Moulis |
| 7,220,270 B2 | 5/2007 | Sawhney et al. |
| 8,282,612 B1 | 10/2012 | Miller |
| 9,078,786 B1 | 7/2015 | Miller |
| 2001/0018577 A1 | 8/2001 | Fitzpatrick et al. |
| 2002/0026157 A1 | 2/2002 | Fournier |
| 2002/0032389 A1 | 3/2002 | Fournier |
| 2002/0082635 A1 | 6/2002 | Kammerer et al. |
| 2002/0111578 A1 | 8/2002 | Buzot |
| 2002/0116070 A1 | 8/2002 | Amara et al. |
| 2003/0073979 A1 | 4/2003 | Naimark et al. |
| 2003/0088190 A1 | 5/2003 | Inoue |
| 2005/0029138 A1 | 2/2005 | Tsaur |
| 2005/0047846 A1 | 3/2005 | Narang et al. |
| 2005/0079156 A1 | 4/2005 | Wong et al. |
| 2005/0101909 A1 | 5/2005 | Rossi |
| 2007/0004995 A1 | 1/2007 | Horn et al. |
| 2007/0014697 A1 | 1/2007 | Sogaro |
| 2007/0066990 A1 | 3/2007 | Marsella et al. |
| 2008/0058767 A1 | 3/2008 | Rotman et al. |
| 2008/0241113 A1 | 10/2008 | Walton et al. |
| 2008/0243103 A1 * | 10/2008 | Whetham ............. A61M 25/10 604/515 |
| 2010/0228239 A1 | 9/2010 | Freed |
| 2013/0110066 A1 | 5/2013 | Sharma et al. |

OTHER PUBLICATIONS

Andrew Pollack, Questioning the Allure of Putting Cells in the Bank, New York Times, pp. 1-5, Jan. 29, 2008. New York, NY.
Schmid et al. "Postpartum hemorrhage: use of hemostatic combat gauze" Amer. J. Obstetrics Gyn. 2012; 206(1). e12-e13.
Scientists Find that Menstrual Blood Stromal Cells Differentiate into Seven Cell Types, GEN News Highlights, p. 1, Apr. 23, 2008. Internet Source.
Non-Final Office Action issued on Aug. 23, 2011 for U.S. Appl. No. 12/399,668, filed Mar. 6, 2009, and granted as U.S. Pat. No. 8,282,612 on Oct. 9, 2012 (Inventor—Miller) (12 pages).
Response to Non-Final Office Action filed on Nov. 23, 2011 for U.S. Appl. No. 12/399,668, filed Mar. 6, 2009, and granted as U.S. Pat. No. 8,282,612 on Oct. 9, 2012 (Inventor—Miller) (15 pages).
Final Office Action issued on Mar. 30, 2012 for U.S. Appl. No. 12/399,668, filed Mar. 6, 2009, and granted as U.S. Pat. No. 8,282,612 on Oct. 9, 2012 (Inventor—Miller) (11 pages).
Response to Final Office Action filed on May 30, 2012 for U.S. Appl. No. 12/399,668, filed Mar. 6, 2009, and granted as U.S. Pat. No. 8,282,612 on Oct. 9, 2012 (Inventor—Miller) (8 pages).
Notice of Allowance issued on Jun. 8, 2012 for U.S. Appl. No. 12/399,668, filed Mar. 6, 2009, and granted as U.S. Pat. No. 8,282,612 on Oct. 9, 2012 (Inventor—Miller) (12 pages).
Issue Notification issued on Sep. 19, 2012 for U.S. Appl. No. 12/399,668, filed Mar. 6, 2009, and granted as U.S. Pat. No. 8,282,612 on Oct. 9, 2012 (Inventor—Miller) (1 page).
Non-Final Office Action issued on Oct. 23, 2014 for U.S. Appl. No. 13/656,516, filed Oct. 19, 2012 and granted as U.S. Pat. No. 9,078,786 on Jul. 14, 2015 (Inventor—Miller) (18 pages).
Response to Non-Final Office Action filed on Jan. 23, 2015 for U.S. Appl. No. 13/656,516, filed Oct. 19, 2012 and granted as U.S. Pat. No. 9,078,786 on Jul. 14, 2015 (Inventor—Miller) (12 pages).
Notice of Allowance issued on Mar. 13, 2015 for U.S. Appl. No. 13/656,516, filed Oct. 19, 2012 and granted as U.S. Pat. No. 9,078,786 on Jul. 14, 2015 (Inventor—Miller) (10 pages).
Issue Notification issued on Jul. 14, 2015 for U.S. Appl. No. 13/656,516, filed Oct. 19, 2012 and granted as U.S. Pat. No. 9,078,786 on Jul. 14, 2015 (Inventor—Miller) (1 page).

* cited by examiner

METHODS AND DEVICES FOR COLLECTING BODY FLUIDS

CROSS REFERENCE TO RELATED APPLICATIONS

This application is a continuation of and claims priority to U.S. patent application Ser. No. 13/656,516, filed Oct. 19, 2012.

TECHNICAL FIELD

The present invention, relates to absorptive devices that are positioned within the uterus, particularly for absorption of bodily fluids.

BACKGROUND OF THE INVENTION

Menstrual bleeding is a part of normal life for women. The onset of menstruation, termed menarche, usually occurs at the age of 12 or 13. The length of a woman's monthly cycle may be irregular during the first one to two years, and may stabilize for many years in a consistent pattern. Once the menstrual cycle stabilizes, a normal cycle may range from 20 to 40 days, with 28 days being an assumed common, average. Age, weight, athletic activity and alcohol consumption are several factors that affect menstrual cycles. For example, younger women (under the age of 21) and older women (over the age of 49) tend to have longer cycle times, generally averaging 31 days and over. Similarly, women who are very thin or athletic also have longer cycles, or no cycles. In contrast, women who consume alcohol on a regular basis tend to have shorter cycle times.

Menstrual fluid is made up of blood and components other than blood, such as endometrial cells, cervical mucus and vaginal secretions. The various inconveniences to women revolting from menstrual bleeding have prompted attempts to regulate or control the outflow of menstrual bleeding. Some sort of pad has been used for centuries, and more recently, newer devices have been proposed. For example, vaginal tampons were introduced a few decades ago. Vaginal tampons are common catamenial devices made of absorbing material and are inserted into the vagina. Due to their absorbent material, tampons absorb fluid upon contact, such as menstrual fluid exiting the cervical canal, and function as reservoirs by delaying the exit of the menstrual fluid from the body.

Tampons present several problems in their use. One problem is that tampons cannot prevent leakage of menstrual fluid all of the time. For example, menstrual fluid may not be absorbed by the tampon because the tampon is saturated, or because the tampon does not provide an adequate seal with the vaginal walls.

Efforts to prevent leakage with tampons have included additional fluid reservoirs added to the tampons, increased absorbency of the absorbent materials found in tampons, use of intravaginal balloons to provide for a better seal, and use of absorbing pads to capture the fluid escaped from the tampon. Super absorbent materials created unforeseen consequences due to prolonged use of a tampon. The materials allowed for the growth of bacteria and led to Toxic Shock Syndrome in those women, using a super absorbent tampon. Toxic shock Syndrome is caused by the toxins released by the bacteria *Staphylococcus aureus*. It is believed that not changing a tampon for a long time can cause staphylococcal bacteria to rapidly multiply, releasing toxins into the bloodstream, leading to the shock syndrome or possible death.

Another catamenial device is the menstrual cup. Generally, a menstrual cup is a cup-shaped intravaginal device for collection of menstrual fluid and is usually made of a flexible material impervious to fluid. The cup is inserted into the vaginal canal to collect menstrual fluid and prevent leakage from the vaginal orifice. It is also generally bulky, necessarily of large diameter, and may be difficult to insert and remove. It has a resilient circular rim significantly larger than the diameter of the vaginal orifice it has to pass through during insertion and during removal. Insertion and removal may be an uncomfortable and difficult task. Furthermore upon removal, it is hard to prevent spillage of the contents.

What is needed are methods and devices that allow for a collection of menstrual fluid that is provided once for each menstrual cycle and does not need to be changed frequently by the individual. Such methods and devices would be leak-proof and may even provide other beneficial purposes.

SUMMARY

The present invention provides methods and devices for intrauterine absorption of fluids, such as collection of menstrual fluid. Methods of the present invention comprise a device as described herein inserted into a uterine cavity of a uterus through a cervical opening. A device of the present invention comprises a central tubing member having a flexible tubing member and an absorbent member attached to at least a portion of the central tubing member. In one embodiment, the central tubing member, the flexible tubing member, and an absorbent member are in a compressed state when the device is inserted into the uterine cavity. For example, the flexible tubing member and the absorbent member are wrapped around, or in close proximity to, the central tubing member prior to insertion, and for ease of insertion. The flexible tubing member and the absorbent member expand from the compressed state to the expanded state by the absorption of fluids present in the uterine cavity. The central tubing member may also expand after absorption of uterine fluids, such as when acting as a reservoir for the fluids. A device which performs methods of the present invention comprises a central tubing member having a flexible tubing member and an absorbable member, both of which are connected to at least one portion of the central tubing member. The absorbable member is also connected to at least one portion of the flexible tubing member. The absorbable member is capable of absorbing menstrual fluid present in the uterus and/or transferring the absorbed menstrual fluid to the flexible tubing member from which the absorbed fluid is transferred into a reservoir portion of the device, such as to the central tubing member.

Methods comprise providing a device of the present invention at a time prior to the onset of the menstrual bleeding period to the uterus, having the device remain in place in the uterus during the menstrual bleeding period, and removal of the device at the cessation of the menstrual bleeding period. While present in the uterus, the device absorbs the menstrual fluids and stores the fluids. The fluids may be retrieved from the device while the device is in position, or after removal, if desired.

Devices of the present invention may provide to the wearer control of her menstrual fluid which does not require hormonal control and may be convenient for women who cannot readily use current methods. For example, women will benefit from devices and methods of the present invention because of the flexibility and convenience. In addition, women who may benefit from such a device include, but are not limited to, women who are in the military or other employment where time for personal hygiene may be limited, women who are not conscious, such as those in a coma, or women who are physically impaired from ease of movement, such as those paralyzed, having severe arthritis or other physical ailments, or women who are mentally incapable of caring for themselves.

Methods comprise use of the collected fluids. The collected fluids may yield blood or blood components, such as red or white blood cells, or blood factors, which may be provided to the wearer or to others. Particular cell types may be isolated from the collected fluids, such as stem cells, and such cell types may have uses which are known in the art, such as for stem cells, regeneration of particular cells. Additionally, the blood collected may be used to support and lessen the strain on the national blood supply. It may be used to supplement and decrease the demand for blood donations. The collected fluids may also be used to monitor or diagnose a physical condition of the wearer.

DETAILED DESCRIPTION

The present invention provides methods and devices for collection of menstrual fluid. Devices and methods of the present invention comprise delivery of a device capable of absorbing and storing uterine fluids. The device is inserted into a uterine cavity of a uterus, for example through a cervical opening. The expandable portions of the device, including, but not limited to, the central tubing member, the flexible tubing member, and an absorbable member, are in a compressed state, for example, the flexible tubing member and the absorbable member are wrapped around the central tubing member, prior to insertion and when first inserted into the uterine cavity. For an example, see FIG. 4. The expandable portions expand from the compressed state to the expanded state, for example by absorbing the fluids that are present in the uterine cavity. For example, the central tubing member may expand in diameter when absorbing or retaining the uterine fluids.

A device of the present invention comprises a central tubing member having a flexible tubing member connected to the central tubing member. The flexible tubing member may be connected to the central tubing member in a region near the proximal end of the central tubing member. For example, the flexible tubing member may be attached near the proximal end of the central, tubing member on the dorsal side of the central tubing member. In one aspect, the central tubing member and the flexible tubing member are fluidly connected such that fluid in the flexible tubing member may outer the central tubing member through at least one opening. The flexible tubing member may have an absorbable member attached to the flexible tubing member that is capable of absorbing or transmitting menstrual and/or other fluids and cells present in the uterus, and may transfer the absorbed menstrual fluid, such as by transfer to the flexible tubing member, and the fluid is then transferred to a reservoir portion of the device. The interior of the central tubing member may comprise a reservoir for such fluids, and cells.

Figure 2:
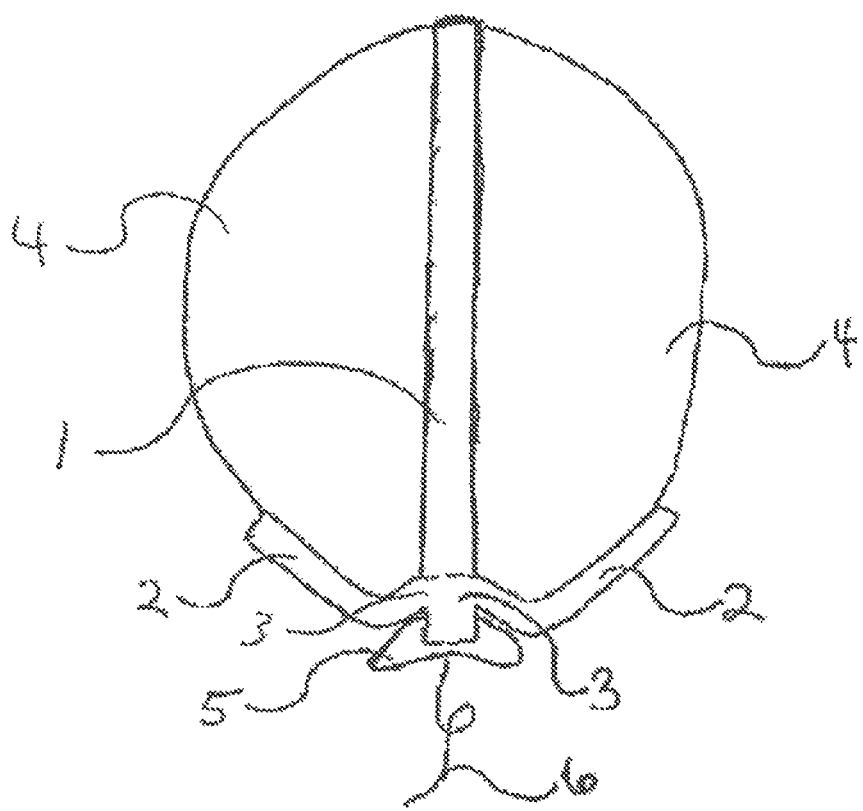
FIG. 2 is a diagram of the reverse view of the embodiment of FIG. 1.
Figure 3:
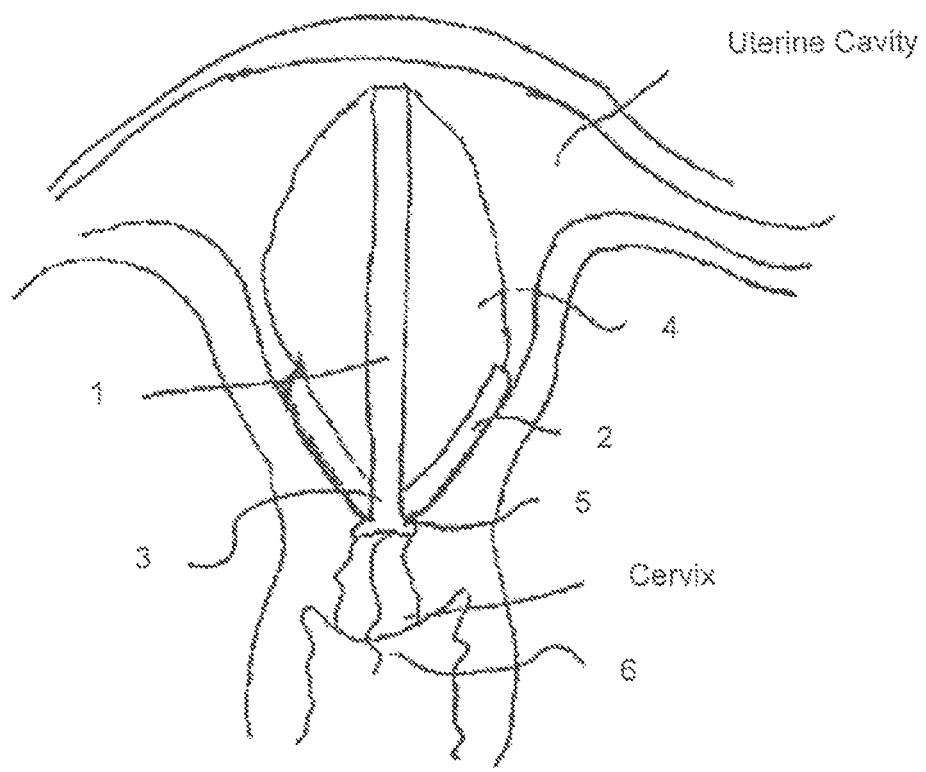
FIG. 3 is a diagram of an embodiment of the present invention placed within a uterus.
Figure 4:
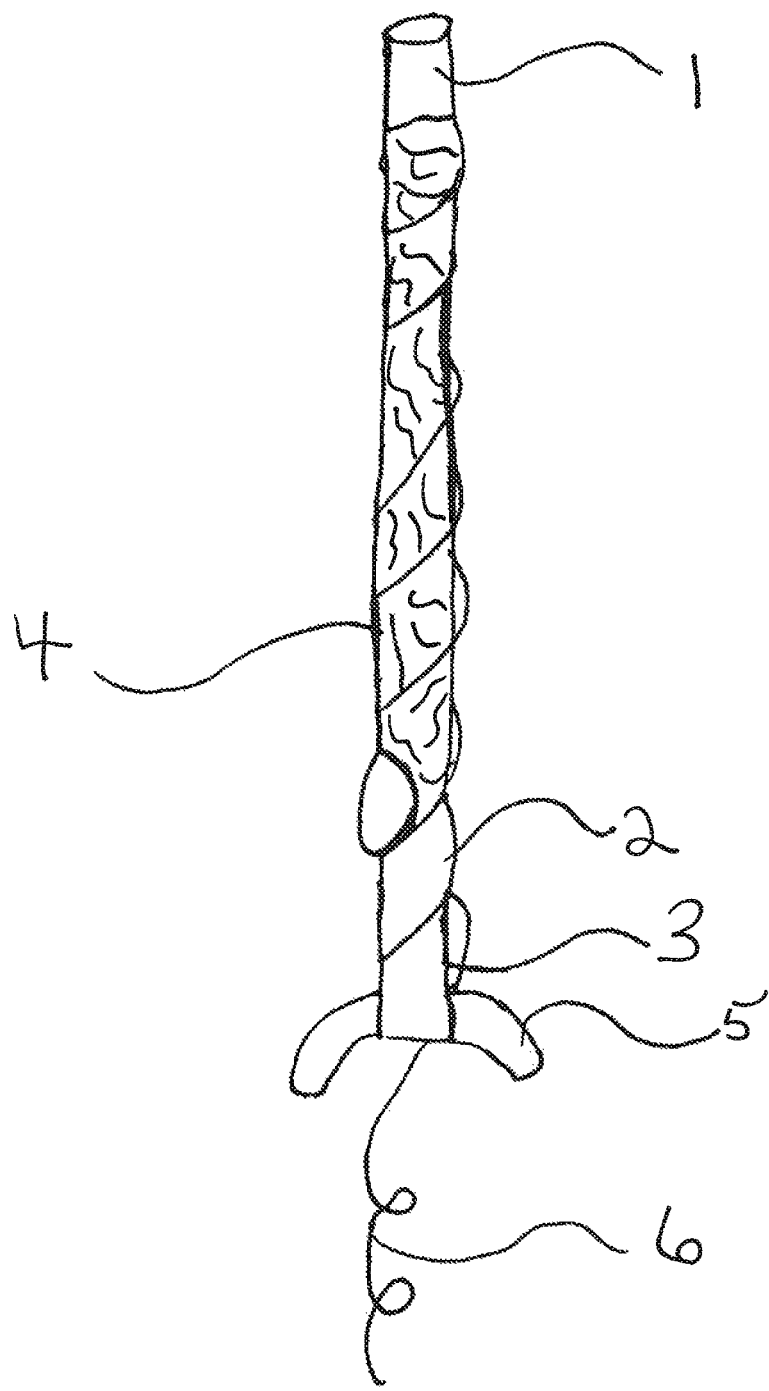
FIG. 4 is a diagram of an embodiment prior to insertion into the uterus.

FIG. 1A shows a device of the present invention, after insertion with the expansion of the absorbable member 4 and the flexible tubing member 2. FIG. 1B shows the device after fluids have been transmitted to the central tubing member 1, and the diameter of the central tubing member 1 has enlarged, for example, from fluid retention in the reservoir in the interior of the central tubing member. FIG. 2 is the view from the back, or the dorsal side, of the device of FIG. 1A. FIG. 3 is a view of the device in place in the uterus, prior to expansion of central tubing member 1. FIG. 4 shows a view of a device prior to insertion into the uterus, when the device is a compressed state.

Figure 1:
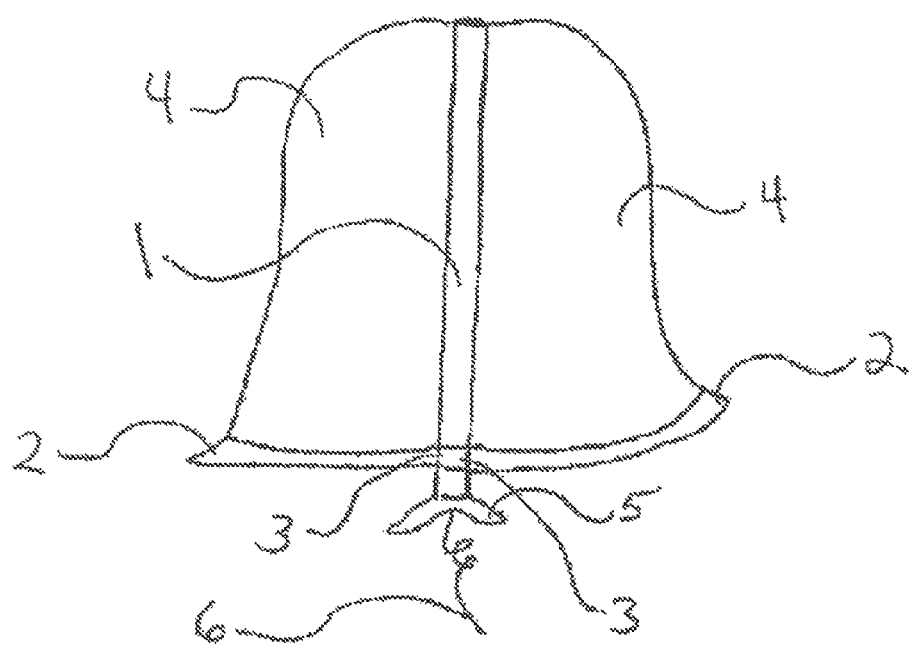
FIGS. 1A and B are diagrams of an embodiment of the present invention.
Figure 1:
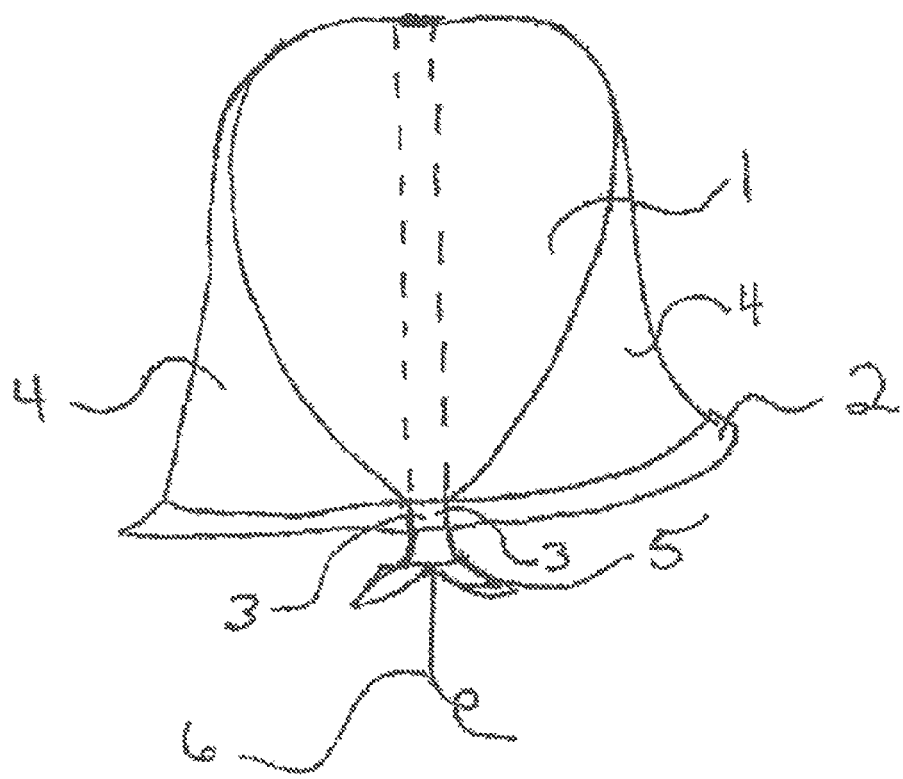

One embodiment of the present invention is shown in FIG. 1. The device comprises a flexible tubing member 2 to which an absorbable member 4 is attached. Prior to insertion into the body, the flexible tubing member 2 and the absorbable member 4 may be wrapped around, or in close association with, the outside of central tubing member 1. The central tubing member 1 may be hollow and function as a reservoir for the collected fluid. The central tubing member may expand in diameter when retaining the uterine fluids, acting as a reservoir, or when absorbing uterine fluids from the flexible tubing-member. On one end, the proximal end, of the central tubing member 1 is found a flexible lip 5. The other end, the distal, end, of the central tubing member 1 is closed to contain the collected fluid within the central tubing member. The proximal end of the central tubing member may be closed, or may have an access site in the proximal end for removal of stored fluids. An access site includes structures that permit access to the interior of the central tubing member, such as seals, self-sealing materials, valves, while the central tubing member contains the stored fluids inside the central tubing member. The central tubing member 1 may be flexible or semi-rigid, and may be made of plastic or any other inert material. The central tubing member 1 may be made of a slowly biodegradable plastic that will begin to degrade in about 60-90 days, and continue to degrade for about 60-120 days. The central tubing member 1 may have absorbent material within it to enable movement of fluid from the flexible tubing member 2 into the central tubing member 1, or to retain the fluid within, the central tubing member.

The flexible tubing member 2 expands laterally and outwardly from the central tubing member 1, once the device is positioned within the uterus. The flexible lubing member 2 is attached to the central tubing member 1 and is in fluid connection with the central tubing member 1 at least a opening 3. In the embodiment shown in FIG. 1A, along the length of the flexible tubing member 2 is attached the absorbable member 4. For example, absorbable member 4 may be a mesh material that absorbs uterine fluids. The absorbable member 1 absorbs the fluids and transfers the absorbed uterine fluids to the flexible tubing member 2. In this embodiment, the portions of the mesh material that contact the flexible tubing member 2 are inserted through the wall of the flexible tubing member 2, so that the absorbed fluids are released from the ends of the mesh material contained within the flexible tubing member 2. As the fluid pools in the flexible tubing member 2, it may create a fluid flow force that moves the final into the central tubing member 1 through opening 3. The fluid may be moved toward and into the central tubing member 1 by absorbent material, using capillary flow, within the flexible tubing member 2 and/or central tubing member 1. As fluid collects within the central tubing member 1, the diameter of the central tubing member 1 may expand to allow for further entry of fluid, or due to absorbance of fluid within the central tubing member 1. In general, the flexible tubing member 2 transmits the fluids to the central tubing member 1, where the fluid is stored until it is removed, or until the entire device is removed.

In an alternative aspect, flexible tubing member 2 may be a tube having a continuous opening, from an end to the attachment point to the central tubing member 1, forming a trough-like flexible tubing member 2. The absorbable member 4 catches the intrauterine fluids and causes the intrauterine fluids to be delivered into the continuous opening. The absorbable member 4 may or may not absorb the fluids, and may form a surface for the fluids to be directed to the trough-like flexible tubing member 2, and from there, into the central tubing member 1.

The absorbable member 4 may be a material that absorbs or does not absorb the intrauterine fluids. The absorbable member 4 may be used to direct fluids to a particular site, such as a continuous opening in flexible tubing member 2. The absorbable member 4 may absorb the fluids, which include any components such as cells, and wick the fluids to or into flexible tubing member 2. The absorbable member 4 is attached to at least a portion of the flexible tubing member 2 and also to at least a portion of the central tubing member 1 (for example, at the distal end of the central, tubing member 1). The absorbable member 4 may contact the flexible tubing member 2 along one or more portions or along the entire length of flexible tubing member 2. The absorbable member 4 may absorb and collect the fluids present, or the absorbable member 4 may absorb and transmit the fluids present to the flexible tubing member 2. Absorbable member 4 may be a sheet of fabric or material that absorbs or directs the fluids and cells of the uterine fluids.

A flexible lip 5 is provided, on the central tubing member 1. When inserted into the uterus, the flexible lip 5 prevents the leakage of uterine fluids by blocking the opening between the uterus and the cervix. See FIG. 3. The flexible lip 5 may also be absorbent to aid in prevention of leakage. The flexible lip 5 may transmit absorbed fluids to central tubing member 1. Indicator 6 may be a string or otter lightweight material, which is attached to the device and is long enough to traverse the vagina so that the wearer has confirmation of the placement of the device and allows for a method of removal of the device.

Methods of the present invention comprise methods of making the devices disclosed herein and methods of use of the devices. Methods of use of the device comprise providing a device described herein to the uterine cavity of a mammal, including a human. A device for collection of uterine fluids may comprise a central tubing member to which a flexible tubing member is attached, and an absorbent member which is attached to the central tubing member of the flexible member, or to both the central tubing member and the flexible member. The device is inserted into the uterine cavity wherein the flexible tubing member and/or the absorbable member may expand or portions of one or both of the flexible tubing member and/or the absorbable member may move away from the central tubing member. For example, the expansion or movement may be due to release of compression of the flexible tubing member and/or the absorbable member, such as after removal of a sheath covering the device prior to insertion (not shown), or may be due to absorption of fluids in the uterine cavity by the flexible tubing member and/or the absorbable member. Once in place in the uterine cavity, the fluids therein may be absorbed and/or transported by the flexible tubing member and/or the absorbable member to the central tubing member, where the fluids are stored. The device may remain in place for a short amount of time, such as 1 to 20 minutes, or may remain in place for 1 day or more than 1 day. A device may remain in the uterine cavity for one to six days or longer, or may remain in place for longer time periods, such as a month or several months. A device may be accessed to remove stored fluids while in place, such as by using a needle, attached to a syringe, to access the proximal end of the central tubing member. For example, a flexible, self-sealing material, may be used to seal the proximal end and this seal may be punctured by a needle, and the fluids stored in the reservoir of the central tubing member removed by action of the syringe, the needle is withdrawn, and the seal closes to retain further collected fluids within the central tubing member. Other methods for accessing the fluid, such as using a needle that mates with a valve in the proximal end of the central tubing member, or other methods, may be used to access the fluid to sample it or to remove it.

The devices of the present invention may be used in methods of collection of menstrual fluids or other uterine fluids. As used herein, fluids includes fluids found within the uterus and or fallopian tubes and cells found therein, including, but not limited to, blood, serum, cellular fluids, uterine lining cells, stem cells, blood cells, immune cells, transformed cells, microorganisms, and fragments of tissue or cells. Such fluids may be collected for the convenience of the wearer of the device. The fluids may be collected for use in detection of substances within the fluids and may be used in methods of monitoring the health status of the wearer of the device. The fluids may contain components that are useful for the wearer of the device or for others. The fluids may contain cells of interest that can be collected and stored for later use by the wearer of the device or others. For example, stem cells are found in menstrual fluid and may be collected, stored or used for the wearer of the device or for others.

The present invention comprises methods of collection of menstrual fluids by a device described herein. The collected fluids may be retained in a reservoir portion of the device. The collected fluids may be retrieved while the device is worn or the fluids may be retrieved after the device is removed from the wearer. The collected fluids may be used in diagnostic assays or other assays or tests to determine or monitor the health status, or status of particular parameters of the wearer. For example, the uterine fluids may be used to monitor the glucose level of the wearer of the device or to monitor one or more hormonal levels of the wearer. The collected fluids may be stored for use by the wearer or others. For example, by collecting the fluid every month, a supply of stem cells could be collected, frozen and stored for use by the wearer.

The devices of the present invention may also be used to collect uterine fluids including, but not limited to, those present at menstruations prior to menstruation, post-menstruation, post menopause, premenarche, perimenopause, post partum, or any time in the life of the mammal. For example, the device may be provided to a female at a time when the female is not menstruating and the fluids present in the uterus at that time are collected. Such collected fluids may be used for monitoring the status of the female or a particular parameter of interest. Cells or fluid collected at that time may be stored and/or used by the female or others.

The devices of the present invention may provide to the wearer control of her menstrual fluid which does not require hormonal control. The devices provide a method of containing menstrual fluids for several days and then disposing of the fluids at a later time. The devices of the present invention may be more convenient for women who do not want to use currently available methods or cannot readily use current methods. For example, women who may benefit from such a device include, but are not limited to, women who are in the military, space flight, or other employment or lifestyles where time or materials are limited for personal hygeine, women who are not conscious, such as those in a coma, or women who are physically impaired from ease of movement, such as those paralyzed, having severe arthritis or other physical ailments, or women who are mentally incapable of caring for themselves. The devices of the present invention may enable women to participate in civilian or military careers that are not currently available to them.

Devices of the present invention may be appropriately sized for wearers. For example, an absorbable member 4 may expand to a diameter of from 3-8 cm, or 2 to about 10 cm, or about 5 cm. A flexible tip 5 may be about 5 mm to 1 cm in diameter and about 5 mm to 1 cm in thickness, and may swell if fluids are absorbed. A central tubing member 1 may be from about 3 cm to about 10 cm, from about 4 cm to about 10 cm, or from about 8 cm. These sixes are for illustration and not to be limiting for the invention.

Methods of the present invention comprise use of the collected fluids. The collected fluids may yield blood or blood components, such as red or white blood cells, or blood factors, which may be provided to the wearer or to others. With a shrinking pool of blood donors and the need for blood donation, the present invention can be used to aid in meeting the critical need for blood or blood components. For example, the collected fluids may be stored and treated in the same ways that venous blood is collected from blood donors. Particular cell types may be isolated from the collected fluids, such as stem cells, and such cell types may have uses which are known in the art, such as for stem cells, regeneration of particular cells. Additionally, the collected fluids may be used to monitor or diagnose a physical condition of the wearer.

It must be noted that, as used in this specification and the appended claims, the singular forms "a," "an," and "the" include plural referents unless the context clearly dictates otherwise.

All patents, patent applications and references included herein are specifically incorporated fey reference in their entireties.

It should be understood, of course, that the foregoing relates only to preferred embodiments of the present invention and that numerous modifications or alterations may be made therein, without departing fern the spirit and the scope of the invention as set forth in this disclosure.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

A menstrual fluid collection device, as shown in FIG. 1 is inserted in the uterus of a 35 year old woman two days prior to the onset of a menstrual period. The device is in place for 10 days and collects the menstrual fluid. No menstrual fluid is lost from the body.

The collection device is removed from the body of the subject and the menstrual fluid in the reservoir is removed. The cellular material is separated from the fluid and both are frozen and stored.

Example 2

A menstrual fluid collection device, as shown in FIG. 1 is inserted in the uterus of a 30 year old woman one day prior to the onset of a menstrual period. The device is in place for 10 days and collects the menstrual fluid. No menstrual fluid is lost from the body. On day 5, the device is accessed and the menstrual fluid present in the reservoir is removed. The cells and fluid are separated. The fluid is used in several diagnostic tests. The cells and the remainder of the fluid are stored.

The collection device is removed from the body of the subject and the menstrual fluid in the reservoir is removed. The cellular material is separated from the fluid and both are frozen and stored.

Example 3

A menstrual fluid collection device, as shown in FIG. 1 is inserted in the uterus of a 25 year old woman one day prior to the onset of a menstrual period. The device is in place for 10 days and collects the menstrual fluid. No menstrual fluid is lost from the body. On day 7, the device is accessed and the menstrual fluid present in the reservoir is removed. The cells and fluid are separated. The blood component is stored an ultimately transferred to local hospitals to supplement blood donations. The cells and the remainder of the fluid are stored.

The collection device is removed from the body of the subject and the menstrual fluid in the reservoir is removed. The cellular material is separated from the fluid and both are frozen and stored.

What is claimed is:

1. A method for collecting stems cells in uterine fluids, comprising:
   a) providing an intrauterine device in a compressed state to an intrauterine cavity of a mammal, the intrauterine device comprising:
      a central tubing member comprising a proximal end and a distal end, wherein the proximal end has at least one opening and the distal end is closed;
      a flexible tubing member connected to the central tubing member in a region near the proximal end of the central tubing member; and
      an absorbent member attached along the length of the flexible tubing member,
      wherein the compressed state of the intrauterine device comprises the flexible tubing member and the absorbent member in close proximity or wrapped around the central tubing member
   b) maintaining the intrauterine device within the intrauterine cavity for more than one day to collect and retain uterine fluids within a reservoir portion located inside the central tubing member;
   c) removing absorbed fluids and cells from the intrauterine device; and
   d) separating the stem cells from the absorbed fluids and cells removed from the intrauterine device.

2. The method of claim 1, wherein the fluids and cells are removed from the intrauterine device while the intrauterine device is in place in the intrauterine cavity.

3. The method of claim 1, wherein the fluids and cells are removed from the intrauterine device after the intrauterine device is removed from the intrauterine cavity.

4. The method of claim 1, wherein the fluid comprises blood, serum, cellular fluids, uterine lining cells, stem cells, blood cells, immune cells, transformed cells, microorganisms, or fragments of tissue or cells.

5. The method of claim 1, wherein the intrauterine device further comprises a flexible lip located at the proximal end of the central tubing member.

6. The method of claim 5, wherein the flexible lip prevents leakage of the fluids.

7. The method of claim 5, wherein the flexible lip is absorbent.

8. The method of claim 7, wherein absorbed fluids from the flexible lip are transmitted to the central tubing member.

9. The method of claim 1, wherein the intrauterine device further comprises an indicator attached near the proximal end of the central tubing member.

10. The method of claim 9, wherein the indicator is a string.

11. The method of claim 1, wherein the fluids absorbed by the absorbent member are transmitted by the flexible tubing member to the reservoir portion of the intrauterine device through at least one opening.

* * * * *